United States Patent
Imhof et al.

(10) Patent No.: US 8,287,549 B2
(45) Date of Patent: Oct. 16, 2012

(54) INSTRUMENT FOR HANDLING A JOINT COMPONENT OF A JOINT PROSTHESIS

(75) Inventors: Martin Imhof, Meggen (CH); Beat Bütler, Streinhausen (CH); René Brack, Cham (CH)

(73) Assignee: Smith and Nephew Orthopaedics AG, Rotkreuz (CH)

( * ) Notice: Subject to any disclaimer, the term of this patent is extended or adjusted under 35 U.S.C. 154(b) by 1027 days.

(21) Appl. No.: 12/065,495

(22) PCT Filed: Aug. 8, 2006

(86) PCT No.: PCT/EP2006/007841
§ 371 (c)(1),
(2), (4) Date: Oct. 24, 2008

(87) PCT Pub. No.: WO2007/025639
PCT Pub. Date: Mar. 8, 2007

(65) Prior Publication Data
US 2009/0248027 A1    Oct. 1, 2009

(30) Foreign Application Priority Data
Aug. 30, 2005    (DE) .......................... 10 2005 041 062

(51) Int. Cl.
*A61B 17/58*    (2006.01)
*A61B 17/60*    (2006.01)
*A61F 2/00*    (2006.01)

(52) U.S. Cl. ....................................................... 606/99

(58) Field of Classification Search ...................... 606/99
See application file for complete search history.

(56) References Cited

U.S. PATENT DOCUMENTS
5,265,840 A  *  11/1993  Gillespie et al. ................... 251/4
2005/0228395 A1 * 10/2005  Auxepaules et al. ........... 606/91

FOREIGN PATENT DOCUMENTS
| DE | 19704577 A1 * | 4/1997 |
| DE | 197 04 577 A1 | 8/1998 |
| DE | 197 22 923 A1 | 8/1998 |
| DE | 101 28 234 A1 | 1/2003 |

OTHER PUBLICATIONS
Machine Translation for DE 19704577 A1.*
German Search Report for PCT/EP2006/007841 dated Nov. 2, 2006.

* cited by examiner

*Primary Examiner* — Thomas Barrett
*Assistant Examiner* — Christine Nelson
(74) *Attorney, Agent, or Firm* — Krieg DeVault LLP

(57) ABSTRACT

An instrument for handling a joint component of a joint prosthesis, which joint component includes a joint surface, includes a grip portion, a suction element in the form of a suction cup with an air-vent opening, the suction cup being placeable in a sealing manner against the joint surface, and a pressure-relief valve associated with the air-vent opening of the suction cup. The pressure-relief valve is coupled to an actuating element which is arranged so as to be movable in the region of the grip surface of the grip portion and, when gripped with one hand, is actuatable with a finger or the thumb of that hand, so that on actuation of the actuating element the valve is lifted away from the air-vent opening.

29 Claims, 1 Drawing Sheet

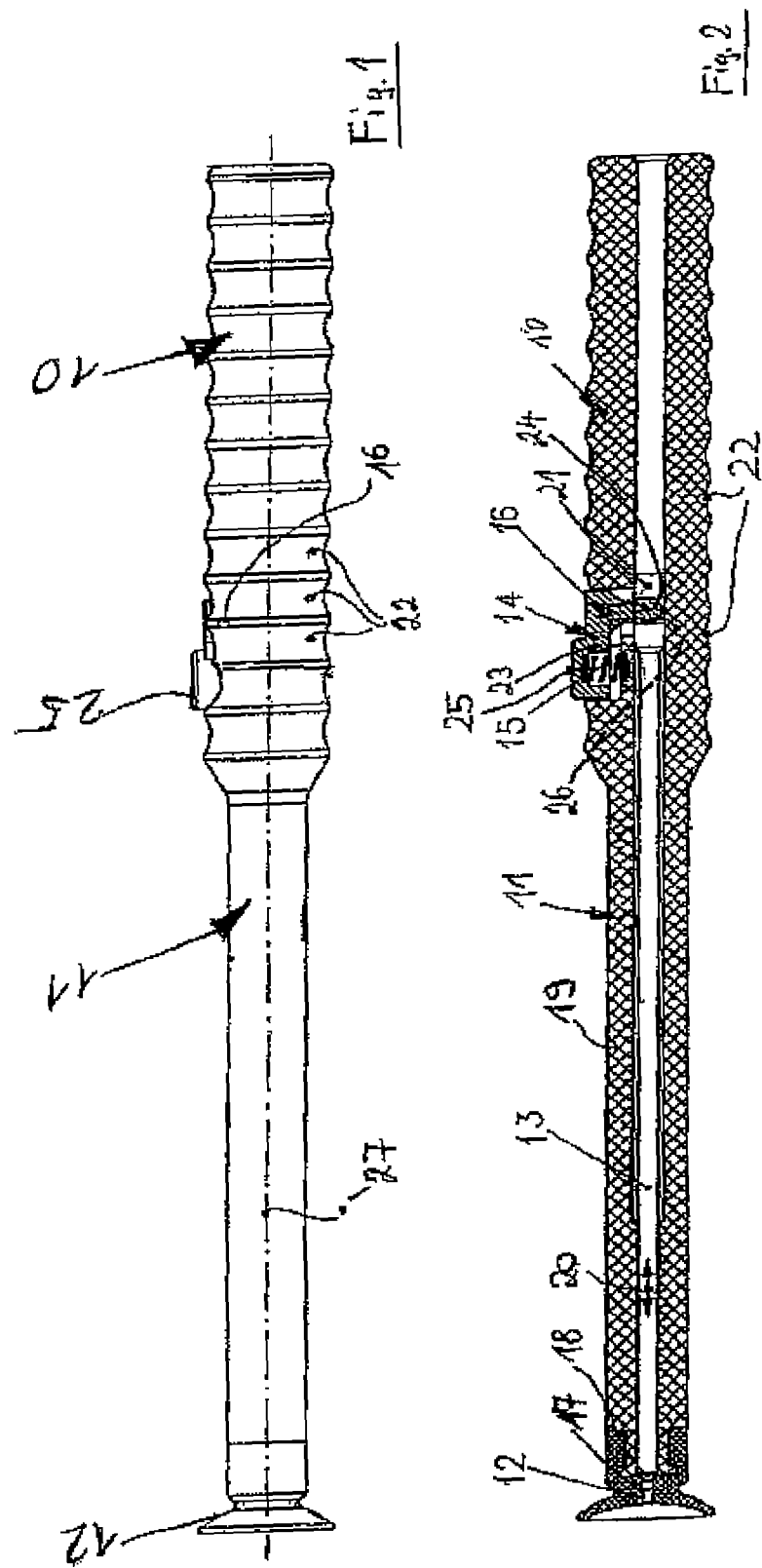

INSTRUMENT FOR HANDLING A JOINT COMPONENT OF A JOINT PROSTHESIS

Cross-Reference to Related Applications

This Application is a US National Phase of the International Application No. PCT/EP2006/007841 filed Aug. 8, 2006 designating the US and published in German on Mar. 8, 2007 as WO/2007/025639, which claims priority of German Patent Application No. 10 2005 041 062.6, filed Aug. 30, 2005.

BACKGROUND OF THE INVENTION

1. Field of the Invention

The invention relates to an instrument for handling a joint component of a joint prosthesis, which joint component includes a joint surface, the instrument having a grip portion, a suction element, in the form of a suction cup with an air-vent opening, placeable in a sealing manner against the joint surface, and a pressure-relief valve associated with the air-vent opening of the suction cup.

2. Description of the Related Art

Such an instrument is known, for example, from DE 101 28 234 A1. However, the instrument disclosed in DE 101 28 234 has a relatively unwieldy mechanism for breaking the partial vacuum in the suction space defined between the joint component surface and the suction cup, the partial vacuum being required in this construction for setting or removing the joint component. Significantly, during handling of the known instrument there is a risk that the partial vacuum in the said suction space will be broken unintentionally, resulting in the disengagement of the joint component from the instrument at an undesirable moment. The reason for this is primarily that the actuating element for the pressure-relief valve projects rearwards axially beyond the grip surface, that is to say in the direction towards the user. Accordingly it cannot be ruled out that the user, when taking hold of the instrument, will inadvertently touch and, undesirably, actuate the actuating element for the pressure-relief valve.

Moreover, with the instrument described above reliable actuation is possible only when using two hands.

A similar situation applies to the setting device according to DE 197 22 923 A1. In that specification too, two-handed operation is mandatory.

SUMMARY OF THE INVENTION

The present invention addresses the problem of developing an instrument of the kind mentioned above so that simple and functionally reliable one-handed operation is possible. The instrument according to the invention should especially be distinguished by its being ergonomic.

That problem is solved according to one embodiment of the invention by an instrument for handling a joint component of a joint prosthesis, which joint component includes a joint surface. The instrument can comprise a grip portion. The instrument can also comprise a suction element in the form of a suction cup with an air-vent opening, said suction cup being configured for placement in a sealing manner against said joint surface. The instrument can also comprise a pressure-relief valve operatively associated with said air-vent opening of said suction cup. The pressure-relief valve is coupled to an actuating element arranged so as to be movable in the region of said grip surface of said grip portion. The actuating element is actuatable, when said grip portion is gripped with one hand, with a finger or the thumb of that hand, to cause said valve to lift away from said air-vent opening. Further structural details and alternative arrangements are described below.

One aspect of an embodiment of the invention is inter alia that the pressure-relief valve is coupled to an actuating element which is arranged so as to be movable in the region of the grip surface of the grip portion and, when gripped with one hand, is actuatable with a finger or the thumb of that hand. The actuating element is located at the level of a fingertip, for example the tip of the index finger or thumb, that is to say in the distal region of the grip surface from the user's point of view. If the grip portion is in the form of a round grip, it is easily grasped with one hand, the actuating element in that case being located at a predetermined distance from the thumb and index finger, preferably about half the length of the index finger or thumb. Accordingly, the actuating element can be actuated without any kind of contorted movements. Actuation of the actuating element lifts the valve away from the air-vent opening, so that ambient air is able to enter the suction space defined by the suction cup on the one hand and the joint surface on the other hand, with the result that the instrument then comes free of the joint surface.

The actuating element can be in the form of a slider or a rocker arm. Furthermore, the actuating element is preferably actuable against the action of a resilient bias on the pressure-relief valve and/or on the actuating element itself That means that the pressure-relief valve is resiliently biased into the closed position. That resilient bias should be capable of being cancelled by the actuating element.

In an alternative arrangement, the actuating element is in the form of a slider which is located in the region of the grip surface and can be displaced parallel thereto.

A preferred embodiment of an instrument constructed in accordance with the invention is described in greater detail below with reference to the accompanying drawings.

BRIEF DESCRIPTION OF THE DRAWINGS

FIG. 1 is a side view of a rod-shaped instrument in accordance with one embodiment of the present invention; and FIG. 2 shows the instrument according to FIG. 1 in longitudinal section.

DETAILED DESCRIPTION OF THE PREFERRED EMBODIMENTS

FIGS. 1 and 2 show, in side view and in longitudinal section, an embodiment of a rod-like instrument 11 for handling a joint component of a joint prosthesis, for example a hip joint prosthesis, which joint component includes a joint surface. The instrument 11 can include a grip portion 10, a suction element in the form of a suction cup 12 with an air-vent opening 17, the suction cup 12 placeable in a sealing manner against the joint surface (not shown herein), and a pressure-relief valve 18 associated with the air-vent opening 17. The pressure-relief valve 18 is part of a valve stem 13. The valve stem 13 is mounted so as to be axially displaceable (see double-headed arrow 20 in FIG. 2) inside a hollow rod 19 arranged between suction cup 12 and grip portion.

The end 21 of the valve stem 13 remote from the suction cup 12 is coupled to an actuating element 14, which is arranged so as to be movable in the region of the grip surface 22 of the grip portion 10 and, when gripped with one hand, is actuatable with a finger or the thumb of that hand, so that on actuation of the actuating element 14 the valve stem 13 and accordingly the valve 18 is lifted away from the air-vent opening 17 of the suction cup 12. In this case, the valve stem 13 is moved to the right in FIG. 2. In the embodiment shown, the actuating element 14 is in the form of a rocker arm, more specifically in the form of a double-armed rocker arm. The rocker arm is mounted so as to be pivotable about an axis 16 extending transverse to the longitudinal direction of the instrument 11. Furthermore, the rocker arm 14 is actuatable against the action of a resilient bias, in this case a helical compression spring 15. As already mentioned, the rocker arm 14, which is mounted so as to be pivotable in the region of the grip portion or the grip surface 22 thereof, is of a double-armed construction, one arm 24 being in operative connection with the valve stem 13 and the other arm 23 having a push-button-like actuating surface 25, which is movable in a direction transverse to the grip surface 22. The mentioned resilient bias of the actuating element 14 is produced by the compression spring 15 arranged between the push-button-like actuating surface 25 and the grip portion 10. The two arms 23, 24 of the double-armed rocker arm 14 are perpendicular to one another, the rocker arm being mounted about the axis 16 so that one arm 23, which includes the push-button-like actuating surface 25, extends approximately parallel to the grip surface 22 or to the longitudinal direction of the instrument 11, and the other arm 24, which is in operative connection with the pressure-relief valve 18 or valve stem 13, extends into the grip surface 22 approximately perpendicularly thereto. The arm 24 of the rocker arm 14 in operative connection with the valve stem 13 engages in a corresponding opening, namely the transverse bore 26 of the valve stem 13. Accordingly, exertion of pressure on the actuating surface 25 of the rocker arm 14 causes the latter to move into the grip surface 22. At the same time, the arm 24 of the rocker arm extending perpendicularly to the grip surface 22 is as a result moved to the right in FIG. 2, accordingly taking with it the valve stem 13 as well as the valve 18 arranged at the distal end thereof, with the result that the air-vent opening 17 is unblocked. Pressure equalization then takes place between the space defined between joint surface and suction cup 12 on the one hand and the external environment on the other hand, that being effected through the hollow rod 19. For that purpose, the valve stem is preferably mounted inside the instrument 11 or the hollow rod 19 with radial play. It is also possible, however, for axially extending air channels to be formed between the valve stem 13 and the hollow rod 19, which channels, when the valve 18 is opened, allow pressure to equalize between the suction space defined between joint surface and suction cup 12 on the one hand and the environment on the other hand. The opening to the external environment is effected either in the region of the mounting of the rocker arm 14 or axially through the grip portion 10.

As already mentioned at the beginning, as an alternative the valve stem 13 can be joined in the region of the grip surface 22 to a slider which is flush with or projects very slightly above the grip surface, which slider is displaceable in the direction of the axial run of the valve stem 13 and approximately parallel to the grip surface 22 against the action of a resilient element, with the result that the pressure-relief valve 18 unblocks the air-vent opening 17.

For setting or removing a joint component or a so-called inlay the partial vacuum between inlay and instrument 11 can be achieved by pressing the instrument 11 with the suction cup 12 against the joint surface. As a result, some of the air located in the space between joint surface and suction cup 12 is expelled from the space, passing by the outer periphery of the suction cup 12. By virtue of its inherent elasticity, the suction cup 12 attempts to press the instrument 11 away from the joint surface again. As a result, in the space defined by the joint surface on the one hand and the suction cup 12 there is produced a partial vacuum by means of which the instrument 11 is held against the joint surface and accordingly against the inlay. Using the instrument 11, the inlay can easily be manipulated (e.g., set in place, rotated or removed again). In order to break the mentioned partial vacuum, the mentioned suction space must be opened to the environment. This can be effected through the air-vent opening 17 as described herein.

It should also be mentioned in connection with the pivot axis 16 of the rocker arm 14 that it can extend radially and spaced apart from the longitudinal centre axis 27 of the instrument 11 and, moreover, closer to the grip surface 22 of the grip portion 10 than to the longitudinal centre axis 27. The actuating surface 25 of the rocker arm 14 can, furthermore, be accessible in the distal region of the grip portion 10, so that actuation can be effected in a trouble-free way when the grip portion 10 is grasped with one hand, that is to say without contorted movements either of the thumb or the index finger.

In the embodiment shown, the grip portion 10 and the hollow rod or hollow shaft 19 are made in one piece, for example from aluminium. The suction cup 12 is mounted at the distal end of the hollow cylinder or shaft 19, and is more specifically slipped over that end (see in this connection DE 101 28 234 A1 or DE 197 08 604 C1). The rocker arm 14 can be made of the same material as the grip portion 10 and the hollow cylinder or shaft 19, that is to say preferably likewise of aluminium. The valve stem 13 including the valve 18, as well as the pivot axis 16, preferably consists of a relatively hard material, for example high-grade steel.

The distal end of the valve stem 13 that defines the pressure-relief valve 18 is approximately semi-spherical and is accordingly self-centering relative to the associated air-vent opening 17. The suction cup 12 consists of a highly elastic material, for example silicone rubber or the like. The valve seat, associated with the pressure-relief valve 18, at the end of the air-vent opening 17 associated with the pressure-relief valve 18 is accordingly also made of that flexible material, with the result that a high degree of sealing is achieved in the closed position of the pressure-relief valve 18 or the associated valve stem 13.

All the features disclosed in the application documents are claimed as being important to the invention insofar as they are novel over the prior art either alone or in combination.

Reference Numerals 10 grip portion
11 instrument
12 suction cup
13 valve stem
14 actuating element (rocker arm)
15 compression spring
16 pivot axis
17 air-vent opening (air-vent bore)
18 pressure-relief valve
19 hollow rod or shaft
20 double-headed arrow
21 proximal end of the valve stem
22 grip surface
23 arm of rocker arm
24 arm of rocker arm
25 push-button-like actuating surface
26 transverse bore
27 longitudinal centre axis

What is claimed is:

1. An instrument for handling a joint component of a joint prosthesis, which joint component includes a joint surface, the instrument comprising:
   a grip portion;

a suction cup with an air-vent opening, said suction cup operatively coupleable in a sealing manner against said joint surface; and a pressure-relief valve operatively associated with said air-vent opening of said suction cup, said valve having a closed position wherein a distal end of said valve is engaged against a valve seat to block said air-vent opening, wherein said pressure-relief valve is coupled to an actuating element arranged so as to be movable in the region of a grip surface of said grip portion, said actuating element being actuatable, when said grip portion is gripped with one hand, with a finger or the thumb of the hand, to cause said valve to lift away from said air-vent opening from said closed position to an open position wherein said distal end of said valve is disengaged from said valve seat to unblock said air-vent opening.

2. The instrument of claim 1, wherein said actuating element is an element selected from the group consisting of a slider and a rocker arm.

3. The instrument of claim 1, wherein the actuating element is actuatable against the action of a resilient bias on at least one of the pressure-relief valve and said actuating element.

4. The instrument of claim 1, wherein said pressure-relief valve is part of a valve stem that is coupled to the actuating element, the valve stem being mounted so as to be axially displaceable between said actuating element and said air-vent opening.

5. The instrument of claim 4, wherein said valve stem comprises high-grade steel.

6. The instrument of claim 4, further comprising, between said grip portion and said suction cup, a hollow rod or shaft, inside which said valve stem is mounted so as to be axially displaceable.

7. The instrument of claim 6, wherein said suction element is slipped over a distal end of the hollow rod or shaft.

8. The instrument of claim 6, wherein said grip portion and said hollow rod or shaft are made in one piece.

9. The instrument of claim 1, wherein said pressure-relief valve is configured to lift upon actuation so as to unblock a fluid connection between said air-vent opening and the external environment.

10. The instrument of claim 1, wherein said valve stem is joined in the region of said grip surface to a slider which is flush with or projects slightly above said grip surface, the slider being displaceable against the action of a resilient element, to cause said pressure-relief valve to unblock said air-vent opening.

11. The instrument of claim 1, wherein said actuating element is located at the level of a fingertip on the grip portion.

12. The instrument of claim 1, wherein said valve seat is defined by said suction cup, and wherein said suction cup including said valve seat is formed of a flexibly elastic material.

13. An instrument for handling a joint component of a joint prosthesis, which joint component includes a joint surface, the instrument comprising:

a grip portion;
a suction cup with an air-vent opening, said suction cup operatively coupleable in a sealing manner against said joint surface; and
a pressure-relief valve operatively associated with said air-vent opening of said suction cup,
wherein said pressure-relief valve is coupled to an actuating element arranged so as to be movable in the region of a grip surface of said grip portion, said actuating element being actuatable, when said grip portion is gripped with one hand, with a finger or the thumb of the hand, to cause said valve to lift away from said air-vent opening, wherein said actuating element is an element selected from the group consisting of a slider and a rocker arm, wherein said rocker arm is mounted so as to be pivotable in the region of said grip surface, and is of double-armed construction, one arm being in operative connection with said pressure-relief valve, while the other arm has a push-button-like actuating surface movable in a direction transverse to said grip surface.

14. The instrument of claim 13, wherein the resilient bias of the actuating element is produced by a compression spring arranged between said push-button-like actuating surface and said grip portion.

15. The instrument of claim 13, wherein the two arms of said double-armed rocker arm are approximately perpendicular to one another, and the rocker arm is mounted so that one arm, which includes said push-button-like actuating surface, extends approximately parallel to the grip surface and the other arm, which is in operative connection with said pressure-relief valve, extends into said grip surface approximately perpendicularly thereto.

16. The instrument of claim 13, wherein said pressure-relief valve is part of a valve stem which is coupled to the actuating element, which valve stem is mounted so as to be axially displaceable between said actuating element and said air-vent opening, the two arms of said double-armed rocker arm are approximately perpendicular to one another, and the rocker arm is mounted so that one arm, which includes said push-button-like actuating surface, extends approximately parallel to the grip surface and the other arm, which is in operative connection with said valve stem, extends into said grip surface approximately perpendicularly thereto.

17. The instrument of claim 16, wherein the arm of said rocker arm in operative connection with said valve stem engages in a transverse bore or other corresponding opening of said valve stem.

18. The instrument of claim 13, wherein said pressure-relief valve has a closed position wherein a distal end of said valve is engaged against a valve seat to block said air-vent opening, and wherein actuation of said actuating element causes said valve to lift away from said air-vent opening from said closed position to an open position wherein said distal end of said valve is disengaged from said valve seat to unblock said air-vent opening.

19. An instrument for handling a joint component of a joint prosthesis, which joint component includes a joint surface, the instrument comprising:

a grip portion;
a suction cup with an air-vent opening, said suction cup operatively coupleable in a sealing manner against said joint surface; and
a pressure-relief valve operatively associated with said air-vent opening of said suction cup,
wherein said pressure-relief valve is coupled to an actuating element arranged so as to be movable in the region of a grip surface of said grip portion, said actuating element being actuatable, when said grip portion is gripped with one hand, with a finger or the thumb of the hand, to cause said valve to lift away from said air-vent opening, wherein said pressure-relief valve is part of a valve stem that is coupled to the actuating element, the valve stem being mounted so as to be axially displaceable between said actuating element and said air-vent opening, wherein a distal end of said valve stem is approximately semi-spherical.

20. The instrument of claim 19, wherein said pressure-relief valve has a closed position wherein a distal end of said valve is engaged against a valve seat to block said air-vent opening, and wherein actuation of said actuating element causes said valve to lift away from said air-vent opening from said closed position to an open position wherein said distal end of said valve is disengaged from said valve seat to unblock said air-vent opening.

21. An instrument for handling a prosthesis, comprising:
   a suction element configured for sealing engagement against a surface of the prosthesis, said suction element having an air vent opening;
   a valve element having a closed position wherein said valve element is engaged against a valve seat to block said air vent opening, said valve element having an open position wherein said valve element is disengaged from said valve seat to unblock said air vent opening; and
   an actuating element operatively coupled to said valve element, wherein actuation of said actuating element transitions said valve element from said closed position to said open position to vent said suction element.

22. The instrument of claim 21, wherein said suction element comprises a suction cup formed of a flexibly elastic material.

23. The instrument of claim 21, wherein said valve seat is defined by said suction element.

24. The instrument of claim 23, wherein said suction element including said valve seat is formed of a flexibly elastic material.

25. The instrument of claim 21, wherein said valve seat is positioned at an end of said air vent opening.

26. The instrument of claim 21, wherein said valve element comprises a valve stem having a distal end engaged against said valve seat in said closed position to block said air vent opening, and wherein said distal end of said valve element is disengaged from said valve seat in said open position to unblock said air vent opening.

27. The instrument of claim 26, wherein said distal end of said valve element is semi-spherical.

28. The instrument of claim 21, further comprising a handle element including a grip portion, said actuating element positioned adjacent a grip surface of said grip portion.

29. The instrument of claim 28, wherein said actuating element comprises a pivotable rocker arm having a first arm operatively coupled with said valve element and a second arm operatively coupled with a push button positioned adjacent said grip surface.

* * * * *